United States Patent [19]

Montgomery

[11] Patent Number: 4,617,190

[45] Date of Patent: Oct. 14, 1986

[54] ENZYMATIC POWDER MILK

[75] Inventor: Robert E. Montgomery, Pacific Palisades, Calif.

[73] Assignee: Laclede Professional Products, Inc., Gardena, Calif.

[21] Appl. No.: 644,395

[22] Filed: Aug. 27, 1984

[51] Int. Cl.$^4$ .............................................. A23C 9/16
[52] U.S. Cl. .................................... 426/61; 426/588; 426/801
[58] Field of Search .................. 426/42, 61, 588, 801, 426/330.3, 334, 335, 63, 64; 424/94; 435/25, 28

[56] References Cited

U.S. PATENT DOCUMENTS

| | | | |
|---|---|---|---|
| 2,717,211 | 11/1952 | Cranston | 426/61 |
| 3,338,719 | 8/1967 | Sawada et al. | 426/61 |
| 4,150,113 | 4/1979 | Hoogendoorn et al. | 424/50 |
| 4,178,362 | 12/1979 | Hoogendoorn et al. | 424/50 |
| 4,269,822 | 5/1981 | Pellico et al. | 425/50 |
| 4,320,116 | 3/1982 | Björck | 424/130 |
| 4,537,764 | 8/1985 | Pellico et al. | 424/49 |
| 4,564,519 | 1/1986 | Pellico et al. | 424/50 |
| 4,576,816 | 3/1986 | Suganuma et al. | 424/50 |
| 4,576,817 | 3/1986 | Montgomery et al. | 424/130 |
| 4,578,265 | 3/1986 | Pellico et al. | 424/50 |

Primary Examiner—Raymond N. Jones
Assistant Examiner—Marianne M. Cintins
Attorney, Agent, or Firm—Donald Diamond

[57] ABSTRACT

Aqueous reconstitutible, powder milk incorporates an enzyme system for providing a bacteriostatic effect upon aqueous reconstitution. The enzyme system contains (a) oxidoreductase enzyme that is hydro-interactable with and specific to oxidizable substrate in the powder milk for producing hydrogen peroxide and (b) peroxidatic peroxidase for interacting with the hydrogen peroxide and oxidizable anion from the powder milk to produce, in the reconstituted milk, oxidized anionic bacterial inhibitor. In an illustrative embodiment, powder milk incorporates (a) glucose oxidase that interacts with glucose in powder milk, upon aqueous dilution, to produce hydrogen peroxide and (b) lactoperoxidase for interacting with hydrogen peroxide and, for example the chloride ion from the powder milk to produce, in the reconstituted milk, the hypochlorite ion, a bacterial inhibitor.

21 Claims, No Drawings

ENZYMATIC POWDER MILK

BACKGROUND OF THE INVENTION

This invention relates to powder milk and, more particularly, to powder milk that incorporates an enzyme system which, upon aqueous dilution of the powder milk, catalyses a reaction sequence that produces a bacteriostatic effect in the reconstituted milk.

The term "powder milk" as used herein refers to dry whole milk, nonfat dry milk and dry food compositions that embody nonfat dry milk as a principal ingredient as, for example, dry infant formula, all of which are adapted to be reconstituted to liquid form by the addition of water.

The food processing industry is continuously striving to make improvements in the quality, safety and storage stability of food products. Enhanced storage stability and shelf life for food products have been attained through improvements in food handling and aseptic packaging as well as through the development and use of safer and more effective preservatives and antioxidants. Where long term storage is sought, techniques for evaporation, lyophilization and freeze-drying of food and beverage products have been shown to be effective. In particular, powder food and beverage products produced by these drying techniques have good storage stability characteristics for extended periods of time, in the absence of exposure to degenerative sources such as moisture, air and light.

Powder food products, upon use, are generally admixed with water to rehydrate the products for consumption. However, the addition of water, while transforming the product to a consumable form, also allows the growth and accumulation of many types of bacteria. These bacteria can be introduced through the water supply that is used to effect rehydration or through ambient sources. In addition, contact with unsanitary containers or utensils can transfer bacterial species to the product. Accordingly, the addition of rehydrating water to powder food products can start a chain of events, concurrent with the introduction of the first bacterium, that can lead to the accumulation of harmful levels of bacteria over a relatively short period of time.

Precautionary steps can be taken to minimize the number and types of potentially harmful pathogens in rehydrated food products. Perhaps the most effective of these, as applicable to the consumer, is the sterilization, by boiling, of the water used to rehydrate the powder food. Although the boiling of water is the most suitable consumer technique for effecting sterilization, it should be noted that even boiling water at 100° C. for 20 minutes will not totally destroy all species of bacterial spores. Alternatively, powder foods and beverages can be preserved with a variety of chemical preservatives such as sodium benzoate or methyl parabenzoic acid. However, at the level allowed for safe ingestion of the preservatives, bacteria can soon overwhelm the exhaustible supply of preservative in the rehydrated product, and subsequently thrive.

In view of the bacteriostatic deficiency associated with the rehydration of powder milk and similar type powder food products, and particularly where rehydration is effected with unboiled or otherwise untreated water, it would be advantageous to provide the powder milk and like products with an ingredient system that is activated upon the addition of water thereto for producing a relatively long-term bacteriostatic environment.

It is disclosed in the patent literature that enzymatic agents can be incorporated into oral products such as toothpaste and chewing gum for producing hydrogen peroxide during oral use.

U.S. Pat. No. 4,150,113 (Hoogendoorn et al., 1979) and U.S. Pat. No. 4,178,362 (Hoogendoorn et al., 1979) disclose, respectively, an enzymatic toothpaste and an enzymatic chewable dentifrice containing glucose oxidase which acts on glucose present in saliva and tooth plaque to produce hydrogen peroxide. The patentees noted that oral bacteria, through enzyme systems having SH-GROUPS, effect glycolysis of food products containing sugars and point out that lactoperoxidase, which is present in saliva, provides the means for transferring oxygen from hydrogen peroxide to the oral bacteria resulting in the oxidation of the SH-containing enzymes into inactive disulfide enzymes. It is further disclosed that the dentifrice may be formulated with potassium thiocyanate.

U.S. Pat. No. 4,269,822 (Pellico et al., 1981) discloses an antiseptic dentifrice containing an oxidizable amino acid substrate and an oxidoreductase enzyme specific to such substrate for producing hydrogen peroxide and ammonia upon oral application of the dentifrice, with pre-application stability being maintained by limiting the quantity of any water present in the dentifrice.

It is also disclosed in the patent literature that enzymatic antibacterial systems can be incorporated into food stuffs and animal feeding stuffs.

U.S. Pat. No. 4,320,116 (Bjorck, 1982) discloses that an enzymatic antibacterial system containing sodium percarbonate, lactoperoxidase and sodium thiocyanate can be incorporated into a dry milk replacer for subsequent aqueous dilution and consumption by calves.

SUMMARY OF THE INVENTION

In accordance with this invention, there is provided an aqueous reconstitutible, powder milk that incorporates an enzyme system for generating a bacteriostatic effect upon aqueous reconstitution, wherein the enzyme system comprises, per gram of powder milk:

(a) from about 0.5 to about 500 International Units of oxidoreductase enzyme that is hydro-interactable with and specific to oxidizable substrate in the powder milk for producing hydrogen peroxide, and (b) from about 0.5 to about 5,000 International Units of peroxidatic peroxidase for interacting with the hydrogen peroxide and oxidizable anion from the powder milk to produce oxidized anionic bacterial inhibitor in the reconstituted milk.

DETAILED DESCRIPTION

The invention described herein is directed to dried milk products which incorporate an enzyme system that is activated upon aqueous reconstitution to provide a bacteriostatic effect in the reconstituted milk.

Dried milk products, the legal definitions thereof, and methods and equipment for making the same are reviewed in *Encyclopedia of Science & Technology*, McGraw-Hill, 1982, Vol. 8 at pp. 567–569.

While this invention can be advantageously used with various powder milk products, it is particularly well suited for use with dry infant formula that typically contains nonfat dry milk, lactose, vegetable fat, vitamins and minerals and, sometimes, additional ingredients which may include dry whey, all in accordance with standards applicable to such products.

The hydro-activated enzyme system comprises oxidoreductase enzyme and peroxidatic peroxidase enzyme. Oxidoreductase enzymes which can be utilized in the practice of this invention and the corresponding oxidizable substrates in powder milk are set forth in the following table:

TABLE A

| OXIDOREDUCTASE ENZYME | OXIDIZABLE SUBSTRATE |
| --- | --- |
| Glucose Oxidase | B-D-glucose |
| Hexose Oxidase | Hexose |
| Galactose Oxidase | D-galactose |
| Pyranose Oxidase | Pyranose |
| Pyruvate Oxidase | Pyruvate |
| Oxalate Oxidase | Oxalate |
| DL-aminoacid Oxidase | DL-aminoacid |

In an illustrative enzymatic reaction, glucose oxidase catalyzes the interaction of Beta-D-glucose, water and oxygen in the aqueous reconstituted milk product to produce hydrogen peroxide and gluconic acid.

Glucose oxidase is characterized in the literature as a glycoprotein containing two molecules of flavine-adenine dinucleotide which has a molecular weight of approximately 150,000, an isoelectric point at pH 4.2 and an optimum pH at 5.5 with a broad pH range from 4 through 7.

The oxidoreductase enzyme is generally present in the powder milk in an amount from about 0.5 to about 500 International Units (hereinafter sometimes abbreviated as IU) per gram of powder milk and, preferably, in an amount from about 2 to about 50 IU per gram of powder milk. The term International Unit(s) identifies that amount of enzyme that will effect catalysis of 1.0 micromole of substrate per minute at pH 7.0 and 25° C. Oxidoreductase enzymes are supplied in dry or liquid form with the label specifying the concentration in International Units on a per gram or per milliliter basis, as appropriate.

In addition to the oxidoreductase enzyme for producing hydrogen peroxide, the enzyme system includes a second enzyme, namely, a peroxidatic peroxidase for interacting with hydrogen peroxide and an oxygen-accepting anion derived from powder milk for producing an oxidized anionic bacterial inhibitor in the reconstituted milk. Peroxidases which can be used in the practice of this invention include lactoperoxidase, myeloperoxidase, chloride peroxidase and iodide peroxidase. The peroxidase is generally present in the powder milk in an amount from about 0.05 to about 5,000 International Units per gram of powder milk and, preferably, in an amount from about 2 to about 100 IU per gram of powder milk.

Oxygen-accepting anions from powder milk include chloride and iodide ions which, in the presence of hydrogen peroxide and peroxidase, are oxidized to hypochlorite and hypoiodite, respectively.

The enzymatic powder milk described herein may be augmented by additionally incorporating into the powder milk supplementary ingredients as, for example, (a) oxidizable substrate specific to the oxidoreductase enzyme utilized in the powder milk, and (b) oxidizable salt such as the thiocyanate, chloride or iodide salt of sodium, potassium, amonium, calcium or magnesium or mixtures of such salts.

The additional oxidizable substrate as, for example, glucose is generally present in the powder milk in an amount from about 0.015 to about 0.6 millimole per gram of powder milk and, preferably, in an amount from about 0.025 to about 0.1 millimole per gram of powder milk. The additional oxidizable salt is generally present in the powder milk in an amount from about 0.0001 to about 0.01 millimole per gram of powder milk and, preferably, from about 0.001 to about 0.006 millimole per gram of powder milk. The term "millimole" identifies that quantity in grams corresponding to the molecular weight of the composition divided by one thousand.

The operable integrity of the enzymatic system can be affected by catalase which is present in commercial glucose oxidase. Catalase, which is extraneous to the enzymatic system of this invention, competes with lactoperoxidase for hydrogen peroxide. In order to reduce loss of hydrogen peroxide through the presence of catalase, an effective amount of an enzymatic inhibitor specific to catalase can be advantageously incorporated into the enzymatic powder milk. An ascorbic salt such as sodium ascorbate, potassium ascorbate, ascorbyl palmitate, or mixtures thereof can be used as an enzymatic inhibitor which is specific to catalase. An effective amount of ascorbic salt for catalase inhibition is from about 0.000001 to about 0.0001 millimole per gram of powder milk.

The enzymatic powder milk of this invention may be formulated with an aminohexose as, for example, an aminoglucose such as glucosamine, N-acetyl glucosamine or mixtures thereof in order to increase the yield or accumulation of oxidized anionic bacterial inhibitor. The aminoglucose is generally present in the enzymatic powder milk in an amount from about 0.0001 to about 0.002 millimole per gram of powder milk and, preferably, in an amount from about 0.0003 to about 0.001 millimole per gram of powder milk.

The enzymatic powder milk can be further formulated with beta-galactosidase which, upon aqueous reconstitution of the powder milk, effects hydrolysis of lactose to galactose and glucose and thereby provides additional oxidizable substrate for producing hydrogen peroxide. This hydrolytic enzyme, beta-galactosidase, can be used in an amount from about 0.5 to about 500 International Units per gram of powder milk.

The enzymes described herein may be advantageously encapsulated to enhance storage stability in the enzymatic powder milk until aqueous reconstitution for consumption or other use. The encapsulating material can be composed of a water soluable polymer or a polymer permeable to a substrate specific to the enzyme or enzymes contained therein. An illustrative encapsulating material is carboxymethylcellulose.

The enzymatic powder milk can be prepared by admixing the oxidoreductase enzyme, peroxidatic peroxidase and optional ingredients with powder milk in a powder blender under conditions of moderate agitation so as not to diminish or otherwise impair the effectiveness of the enzymes.

EXAMPLE I

This example illustrates the bacteriostatic effect in hydro-reconstituted dry infant formula that incorporates the enzymatic system of this invention. Enfamil dry infant formula, a powder milk composition based on nonfat dry milk, was used for this evaluation.

800 grams of Enfamil powder were admixed with 4,000 IU of glucoseoxidase (40 mg at 100 IU/mg) and 4,000 IU of lactoperoxidase (40 mg at 100 IU/mg). 432 grams of the enzymatic Enfamil powder were mixed with and dissolved in 1.0 liter of water containing a phosphate buffer to maintain the pH between 6 and 7. Five samples of reconstituted, enzymatic powder milk were prepared in this manner. To provide a control, five additional samples of reconstituted, Enfamil powder milk were prepared in a like manner except that the Enfamil powder was not modified by enzyme addition.

The following organisms were used in this evaluation:
(a) *Staphylococcus aureus* (ATCC 6538)
(b) *Salmonella cholerasius* (ATCC 10708)
(c) *Escherichia coli* (ATCC 25923)
(d) *Candida albicans* (ATCC 10231)
(e) *Lactobacillus plantarum* (ATCC 8014)

Each of the above designated organisms was inoculated into a 20 ml tryptic soy broth and incubated at 35° C. for 24 hours. Each of the resulting cultures was washed 3 times with phosphate buffer solution by centrifugation. Each of the cell suspensions from centrifugation was diluted 1:10 and 20 microliters were inoculated into a screw cap tube containing 20 ml of the reconstituted, enzymatic Enfamil powder milk. The inoculated samples were incubated at 25°–30° C. for the duration of the test. As plating medium, tryptic soy agar was used for *S. aureus, S. cholerasius,* and *E. coli,* and Sabouraud dextrose agar was used for *C. albicans,* and Lactobacilli agar was used for *L. plantarum*. Plates were incubated at 32°–35° C. for 48 hours aerobically except for *L. plantarum* which was incubated under increased carbon dioxide tension (candle jar). Counts of the sample and control were taken every hour initially up to 8 hours and then every 8 hours thereafter. The results for Enfamil powder milk that incorporates the enzyme system of this invention are set forth in TABLE I while the results for unmodified Enfamil powder milk are set forth in TABLE Ia:

TABLE I

ENZYMATIC POWDER MILK

| Time, hr | C. albicans | L. plantrum | S. aureus | E. coli | S. cholerasius |
|---|---|---|---|---|---|
| 0 | $8.2 \times 10^4$ | $8.8 \times 10^4$ | $2.8 \times 10^5$ | $1.0 \times 10^5$ | $2.9 \times 10^5$ |
| 1 | $7.4 \times 10^4$ | $5.1 \times 10^4$ | $2.6 \times 10^5$ | $1.1 \times 10^5$ | $2.0 \times 10^5$ |
| 2 | $9.5 \times 10^4$ | $6.5 \times 10^4$ | $1.4 \times 10^5$ | $8.4 \times 10^4$ | $1.6 \times 10^5$ |
| 3 | $6.5 \times 10^4$ | $5.9 \times 10^4$ | $1.0 \times 10^5$ | $1.1 \times 10^5$ | $1.8 \times 10^5$ |
| 4 | $7.7 \times 10^4$ | $5.6 \times 10^4$ | $1.1 \times 10^5$ | $1.9 \times 10^5$ | $2.7 \times 10^5$ |
| 5 | $5.3 \times 10^4$ | $6.5 \times 10^4$ | $8.5 \times 10^4$ | $1.9 \times 10^5$ | $2.3 \times 10^3$ |
| 6 | $7.2 \times 10^4$ | $7.0 \times 10^4$ | $8.0 \times 10^4$ | $2.4 \times 10^5$ | $2.5 \times 10^5$ |
| 7 | $6.8 \times 10^4$ | $8.0 \times 10^4$ | $5.0 \times 10^4$ | $3.4 \times 10^5$ | $1.7 \times 10^4$ |
| 8 | $7.7 \times 10^4$ | $8.3 \times 10^4$ | $6.0 \times 10^4$ | $1.0 \times 10^5$ | $1.4 \times 10^4$ |
| 16 | $3.3 \times 10^4$ | $6.8 \times 10^4$ | $1.0 \times 10^4$ | $1.2 \times 10^7$ | $4.1 \times 10^4$ |
| 24 | $3.0 \times 10^4$ | $4.3 \times 10^4$ | $1.1 \times 10^4$ | $1.0 \times 10^5$ | 20 |
| 32 | $2.1 \times 10^4$ | <3000 | 30 | 130 | <10 |
| 40 | $2.4 \times 10^4$ | <200 | 10 | 10 | <10 |
| 48 | $8.0 \times 10^3$ | <10 | <10 | <10 | 10 |

TABLE Ia

UNMODIFIED POWDER MILK

| Time, hr | C. albicans | L. plantrum | S. aureus | E. coli | S. cholerasius |
|---|---|---|---|---|---|
| 0 | $8.2 \times 10^4$ | $8.8 \times 10^4$ | $2.8 \times 10^5$ | $1.0 \times 10^5$ | $2.9 \times 10^5$ |
| 1 | $8.0 \times 10^4$ | $6.9 \times 10^4$ | $3.3 \times 10^5$ | $1.1 \times 10^5$ | $3.2 \times 10^5$ |
| 2 | $7.7 \times 10^4$ | $1.1 \times 10^5$ | $2.6 \times 10^5$ | $1.2 \times 10^5$ | $3.1 \times 10^5$ |
| 3 | $1.1 \times 10^5$ | $6.9 \times 10^4$ | $3.3 \times 10^5$ | $2.3 \times 10^5$ | $4.4 \times 10^5$ |
| 4 | $6.6 \times 10^4$ | $8.0 \times 10^4$ | $6.6 \times 10^5$ | $9.5 \times 10^5$ | $2.0 \times 10^6$ |
| 5 | $1.5 \times 10^5$ | $2.1 \times 10^5$ | $6.7 \times 10^5$ | $2.6 \times 10^6$ | $2.6 \times 10^6$ |
| 6 | $1.3 \times 10^5$ | $3.0 \times 10^5$ | $1.2 \times 10^6$ | $2.0 \times 10^7$ | $5.3 \times 10^6$ |
| 7 | $3.0 \times 10^5$ | $4.8 \times 10^5$ | $1.0 \times 10^6$ | $3.3 \times 10^7$ | $2.0 \times 10^7$ |
| 8 | $1.0 \times 10^5$ | $4.5 \times 10^5$ | $1.2 \times 10^6$ | $5.1 \times 10^7$ | $3.7 \times 10^7$ |

TABLE Ia-continued

UNMODIFIED POWDER MILK

| Time, hr | C. albicans | L. plantrum | S. aureus | E. coli | S. cholerasius |
|---|---|---|---|---|---|
| 16 | $3.2 \times 10^5$ | $1.0 \times 10^7$ | $2.2 \times 10^7$ | $1.0 \times 10^9$ | $1.2 \times 10^9$ |
| 24 | $7.0 \times 10^5$ | $8.7 \times 10^7$ | $5.0 \times 10^7$ | $1.8 \times 10^9$ | $3.0 \times 10^9$ |
| 32 | $6.4 \times 10^5$ | $2.3 \times 10^8$ | $5.4 \times 10^7$ | $2.0 \times 10^9$ | $3.0 \times 10^9$ |
| 40 | $4.1 \times 10^6$ | $2.4 \times 10^8$ | $7.0 \times 10^7$ | $1.3 \times 10^9$ | $1.4 \times 10^9$ |
| 48 | $2.0 \times 10^6$ | $1.1 \times 10^9$ | $1.3 \times 10^9$ | $1.2 \times 10^9$ | $1.3 \times 10^9$ |

As shown by the results set forth in TABLES I and Ia, the control samples (reconstituted Enfamil powder milk) showed proliferation of each of the organisms during the test, whereas the enzyme modified samples (reconstituted, enzymatic Enfamil powder milk) began to show a decrease in the concentration of viable microorganisms within 24 hours, and this decrease continued over the remainder of the 48 hour test period.

EXAMPLE II

Formulation 2a illustrates a dry infant formula that incorporates glucose oxidase and lactoperoxidase.

| INGREDIENTS | 2a AMOUNT |
|---|---|
| Nonfat dry milk | 900 g |
| Lactose | 60 g |
| Corn Oil | 30 g |
| Coconut Oil | 7 g |
| Vitamins and Minerals | 3 g |
| Glucose oxidase | 3,000 IU (30 mg at 100 IU/mg) |
| Lactoperoxidase | 2,000 IU (20 mg at 100 IU/mg) |

Formulation 2b illustrates a dry infant formulation that incorporates the enzyme system together with a metal salt of an oxygen-accepting anion.

| INGREDIENTS | 2b AMOUNT |
|---|---|
| Nonfat dry milk | 900 g |
| Lactose | 60 g |
| Glucose | 20 g |
| Corn Oil | 10 g |
| Coconut Oil | 7 g |
| Vitamins and Minerals | 3 g |
| Glucose oxidase | 5,000 IU (50 mg at 100 IU/mg) |
| Myleoperoxidase | 1,000 IU (10 mg at 100 IU/mg) |
| Potassium thiocyanate | 150 mg (150 ppm) |

Formulation 2c illustrates a dry milk composition for calves that incorporates the enzyme system.

| INGREDIENTS | 2c AMOUNT |
|---|---|
| Nonfat dry milk | 600 g |
| Whey powder | 35 g |
| Ground corn | 150 g |
| Corn Oil | 50 g |
| Corn starch | 30 g |
| Raw sugar | 25 g |
| Glucose | 60 g |
| Vitamins and Minerals | 50 g |
| Glucose oxidase | 6,000 IU (60 mg at 100 IU/mg) |
| Lactoperoxidase | 2,000 IU (20 mg at 100 IU/mg) |

Formulation 2d illustrates an enzymatic powder milk that can be used in the preparation of a low lactose, reconstituted milk.

| INGREDIENTS | 2d AMOUNT |
|---|---|
| Nonfat dry milk | 850 g |
| Glucose | 50 g |
| Corn Starch | 50 g |
| Corn Oil | 30 g |
| Coconut Oil | 10 g |
| Vitamins and Minerals | 10 g |
| Amyloglucosidase | 1,000 IU (100 mg at 10 IU/mg) |
| Glucose oxidase | 5,000 IU (50 mg at 100 IU/mg) |
| Iodide peroxidase | 3,500 IU (35 mg at 100 IU/mg) |

Formulation 2e illustrates an electrolyte formula for livestock where fluid loss is a consideration. The dilution is approximately 28 grams of powder per liter of water.

| INGREDIENTS | 2e AMOUNT |
|---|---|
| Nonfat dry milk | 500 g |
| Potassium chloride | 5 g |
| Sodium chloride | 100 g |
| Sodium bicarbonate | 75 g |
| Glucose | 320 g |
| Glucose oxidase | 1,000 IU (10 mg at 100 IU/mg) |
| Chloride peroxidase | 1,000 IU (10 mg at 100 IU/mg) |
| Myeloperoxidase | 2,000 IU (20 mg at 100 IU/mg) |

In view of the foregoing description and examples, it will become apparent to those of ordinary skill in the arts that equivalent modifications thereof may be made without departing from the spirit and scope of this invention.

That which is claimed is:

1. Aqueous reconstitutible, powder milk that incorporates an enzyme system for generating a bacteriostatic effect upon aqueous reconstitution, said enzyme system comprising, per gram of power milk:
   (a) from about 0.5 to about 500 International Units of oxidoreductase enzyme that is hydro-interactable with and specific to oxidizable substrate in the powder milk for producing hydrogen peroxide, and
   (b) from about 0.05 to about 5,000 International Units of peroxidatic peroxidase for interacting with said hydrogen peroxide and oxidizable anion from the powder milk to produce an oxidized anionic bacterial inhibitor in the reconstituted milk.

2. The powder milk of claim 1 wherein the concentration of oxidoreductase enzyme is from about 2 to about 50 International Units and the concentraton of peroxidatic peroxidase is from about 2 to about 100 International Units.

3. The powder milk of claim 1 wherein the oxidoreductase enzyme is glucose oxidase.

4. The powder milk of claim 1 wherein the oxidoreductase enzyme is galactose oxidase.

5. The powder milk of claim 1 wherein the oxidoreductase enzyme is pyranose oxidase.

6. The powder milk of claim 1 wherein the peroxidatic peroxidase is lactoperoxidase.

7. The powder milk of claim 1 wherein the peroxidatic peroxidase is myeloperoxidase.

8. The powder milk of claim 1 wherein the peroxidatic peroxidase is chloride peroxidase.

9. The powder milk of claim 1 wherein the peroxidatic peroxidase is iodide peroxidase.

10. The powder milk of claim 1 wherein the oxidoreductase enzyme is glucose oxidase and the peroxidatic enzyme is lactoperoxidase.

11. The powder milk of claim 1 which contains additional oxidizable substrate specific to oxidoreductase enzyme incorporated into said powder milk for producing hydrogen peroxide, said additional substrate being present in an amount from about 0.015 to about 0.6 millimole per gram of powder milk.

12. The powder milk of claim 11 wherein the concentration of additional substrate is from about 0.025 to about 0.1 millimole per gram of powder milk.

13. The powder milk of claim 1 wherein the additional substrate is glucose and the oxidoreductase enzyme is glucose oxidase.

14. The powder milk of claim 1 which contains, as an additional component per gram of powder milk, from about 0.0001 to about 0.01 millimole of a metal salt of an oxygen accepting anion selected from the group consisting of thiocyanate, chloride and iodide or a mixture of such salts.

15. The powder milk of claim 14 wherein the concentration of the metal salt is from about 0.001 to about 0.006 millimole per gram of powder milk.

16. The powder milk of claim 14 wherein the metal salt is potassium thiocyanate.

17. The powder milk of claim 14 wherein the metal salt is an alkali metal chloride.

18. The powder milk of claim 14 wherein the metal salt is an alkali metal iodide.

19. The powder milk of claim 1 which additionally contains an effective amount of an enzymatic inhibitor specific to catalase.

20. The powder milk of claim 19 wherein the enzymatic inhibitor specific to catalase is an ascorbate salt in an amount from about 0.000001 to about 0.0001 millimole per gram of powder milk.

21. The powder milk of claim 1 which also contains from about 0.5 to about 500 International Units of beta-galactosidase per gram of powder milk.

* * * * *